US008168763B2

(12) United States Patent
Kopacek et al.

(10) Patent No.: US 8,168,763 B2
(45) Date of Patent: May 1, 2012

(54) FERRITIN 2 FOR THE HOST IMMUNIZATION AGAINST TICKS

(75) Inventors: Petr Kopacek, Ledenice (CZ); Ondrej Hajdusek, Ceske Budejovice (CZ)

(73) Assignee: Biology Centre AS CR, V.V.I., Ceske Budejovice (CZ)

( * ) Notice: Subject to any disclaimer, the term of this patent is extended or adjusted under 35 U.S.C. 154(b) by 0 days.

(21) Appl. No.: 13/000,813

(22) PCT Filed: Jun. 18, 2009

(86) PCT No.: PCT/CZ2009/000085
§ 371 (c)(1),
(2), (4) Date: Jan. 28, 2011

(87) PCT Pub. No.: WO2009/155886
PCT Pub. Date: Dec. 30, 2009

(65) Prior Publication Data
US 2011/0118449 A1    May 19, 2011

(30) Foreign Application Priority Data
Jun. 25, 2008   (CZ) ............................... PV 2008-402

(51) Int. Cl.
*C07K 14/435* (2006.01)
(52) U.S. Cl. ....................................................... 530/400
(58) Field of Classification Search .................. None
See application file for complete search history.

(56) References Cited

PUBLICATIONS

Kopacek, Petr et al, Insect Biochemistry and Molecular Biology, vol. 33, pp. 103-113, 2003, Molecular cloning, expression and isolation of ferritins from two tick species-*Ornithodoros moubata* and *Ixodes ricinus*.*
Long, Joanne C et al, Fer1 and Fer2 encoding two ferritin complexes in *Chlamydomonas reinhardtii* Chloroplkasts are regulated by iron, Genetics, vol. 179, pp. 137-147, May 2008.*
Xu, G e tal, Genetics, Ferritin Gene Coding Sequences are conserved among eight hard tick species (*Ixodida:Ixodidae*), Annals of the Entomological Society of America, vol. 97(3), pp. 567-573, 2004.*
Jongejan et al, Advances in the genomics of ticks and tick-borne pathogens, Trends in Parasitology, vol. 23(9), pp. 391-396, 2007.*
Letter from Beetz & Partner to European Patent Office in Reply to Written Opinion date Apr. 29, 2011, pp. 1-3.
International Search Report of International Application No. PCT/CZ2009/00085, pp. 1-4, Jan. 18, 2010.
Written Opinion of International Application No. PCT/CZ2009/000085, pp. 1-6, Jan. 5, 2011.

* cited by examiner

*Primary Examiner* — Albert Navarro
*Assistant Examiner* — Ginny Portner
(74) *Attorney, Agent, or Firm* — Notaro, Michalos & Zaccaria P.C.

(57) ABSTRACT

Ferritin 2 is a tick secreted protein, which serves in the tick plasma as a non-heme iron transporter from the gut to the peripheral tissues. It can be exploited as an antigen for raising up host antibodies, which can reversely block this antigen in the tick and the attached tick will not have functional mechanism of the non-heme iron transport from the gut to the peripheral tissues. This mechanism is essential for the further tick development and its blocking eventually prevents transmission of tick-borne pathogens.

3 Claims, 1 Drawing Sheet

FER2-IR  z *Ixodes ricinus* without the signal sequence
GNNLFENLDKYPLQDECQAALQEHINVEMHASLVYMQMAAHFDNNKVARKGFSTFFA
ENSKEEREHAQKIIDYINKRGSTVSLVNIDMPLITTWKSVLQALRDAISLENKVTNKLHA
VHKIADEECKDPQLMDFIESEFLEEQVNSIDKLQRMITVLSNMDSGTGEYLLDRELLGD
KKEF (SEQ. ID. NO: 1).

FER2-IS z *Ixodes scapularis*
GNNLFENLDKYPLQDECQAALQEHINVEMHASLVYMQMAAHFDNNKVARKGFSTFFA
ENSKEEREHAQKIIDYINKRGSTVSLVNIDMPQITTWKSVLQALRDAISLENKVTNKLHA
VHKTADEECKDPQLMDFIESEFLEEQVTSIDKLQRMITVLSNMDSGTGEYLLDRELLGD
KKEF (SEQ. ID. NO: 2).

FER2-RM z *Rhipicephalus microplus*
GNNLNDQVNKYILPDRCRAGLQEQLNLELHASLVYMQMAAHLANNKVARGGFARFFR
DQSSEEREHAQKIIDYLNLRGGTVSAVNVDMPPTAIWMSVLDALQAALALEHRVTNRL
YELHRLAEEYDAQMADFLEQEFLAEQVRSIDQLQRLITQLQNMETGLGEFLLDQQLRA
(SEQ. ID. NO: 3).

FER2-DV z *Dermacentor variabilis*
GNNLNEQVNQNRYFLHDRCRIGLQEQVNLELHASLVYMQMAAHLANNKVARNGFARF
FRDQSSEEREHAQKLVDYVNLRGGTVSAVSVDMPATATWMSVLDALQAALALEHRVT
NRLHELHRLADDSQDPQMADFLEQEFLAEQVRSIDQLQRLITQLQNMDTGLGEFLLDQ
QLRA (SEQ. ID. NO: 4).

FER2-IR z *Ixodes ricinus* without the signal sequence
GNNLFENLDKYPLQDECQAALQEHINVEMHASLVYMQMAAHFDNNKVARKGFSTFFA
ENSKEEREHAQKIIDYINKRGSTVSLVNIDMPLITTWKSVLQALRDAISLENKVTNKLHA
VHKIADEECKDPQLMDFIESEFLEEQVNSIDKLQRMITVLSNMDSGTGEYLLDRELLGD
KKEF (SEQ. ID. NO: 1).

FER2-IS z *Ixodes scapularis*
GNNLFENLDKYPLQDECQAALQEHINVEMHASLVYMQMAAHFDNNKVARKGFSTFFA
ENSKEEREHAQKIIDYINKRGSTVSLVNIDMPQITTWKSVLQALRDAISLENKVTNKLHA
VHKTADEECKDPQLMDFIESEFLEEQVTSIDKLQRMITVLSNMDSGTGEYLLDRELLGD
KKEF (SEQ. ID. NO: 2).

FER2-RM z *Rhipicephalus microplus*
GNNLNDQVNKYILPDRCRAGLQEQLNLELHASLVYMQMAAHLANNKVARGGFARFFR
DQSSEEREHAQKIIDYLNLRGGTVSAVNVDMPPTAIWMSVLDALQAALALEHRVTNRL
YELHRLAEEYDAQMADFLEQEFLAEQVRSIDQLQRLITQLQNMETGLGEFLLDQQLRA
(SEQ. ID. NO: 3).

FER2-DV z *Dermacentor variabilis*
GNNLNEQVNQNRYFLHDRCRIGLQEQVNLELHASLVYMQMAAHLANNKVARNGFARF
FRDQSSEEREHAQKLVDYVNLRGGTVSAVSVDMPATATWMSVLDALQAALALEHRVT
NRLHELHRLADDSQDPQMADFLEQEFLAEQVRSIDQLQRLITQLQNMDTGLGEFLLDQ
QLRA (SEQ. ID. NO: 4).

FERRITIN 2 FOR THE HOST IMMUNIZATION AGAINST TICKS

CROSS-REFERENCE TO RELATED APPLICATIONS

This is a national-stage application, claiming priority from International Application No. PCT/CZ2009/000085, filed Jun. 18, 2009, which application, in turn, claims priority from Czech Republic Application No. PV 2008-402, filed Jun. 25, 2008.

BACKGROUND OF THE INVENTION

Field of the Invention

The present invention relates to a protein antigen for immunization of the organism—the produced antibody will block an iron transport in the tick body and hereby prevent its long-lasting feeding on the host, eventually block transmission of pathogens from the tick to the host.

Until now, only intracellular ferritin 1 has been known in ticks, which was isolated, cloned and sequenced in our laboratory for the first time from two tick species—*Ixodes ricinus* and *Ornithodoros moubata*. Later on, other orthologs of ferritin 1 were sequenced and partially characterized from other tick species in different laboratories. Tick ferritin 1 is post-trascriptionally regulated by the IRP (iron-regulatory protein), which binds IRE (iron-responsive element) loop of the particular mRNA. Ferritin 1 is an oligomer (composed of 24 subunits) and functions in the intracellular iron storage and prevention of the undesirable oxidative effects caused by the free iron.

BRIEF DESCRIPTION OF THE FIGURES

FIG. 1 is a list of the amino acid sequences of Ferritin 2 disclosed herein.

DETAILED DESCRIPTION OF THE PREFERRED EMBODIMENTS

Ferritin 2 is a newly identified and characterized protein, which is secreted into the tick plasma. It has been identified in ticks *Ixodes ricinus, Ixodes scapularis, Dermacentor variabilis*, and *Rhipicephalus microplus* (formerly *Boophilus microplus*). We have sequenced these ferritins and determined their primary structures. Ferritin 2 functions in the tick body as a transporter of iron, which is obtained from the host blood (plasma). When we succeed to block the protein, the attached tick will not be able to feed on the host, because the mechanism of non-heme iron transport from the gut to the peripheral tissue will not be functional, which is essential for tick parasitic life. The blocking of ferritin 2 can be achieved by the reaction with the specific antibody, what leads to the formation of immunocomplex. Specific antibodies will be raised up in the host organism after immunization with the tick antigen ferritin 2. A recombinant ferritin 2 or its fragment expressed in the prokaryotic (*Escherichia coli*, etc.), or eukaryotic (*Pichia pastoris*, insect cells, etc.) expression systems can be used as a suitable antigen for the immunization. Expressed and purified recombinant ferritin 2 could be used for immunization with the appropriate adjuvants or formulation media. The advantage of use of ferritin 2 is its substantial amino-acid sequence difference from the mammalian heavy (H) or light (L) chain ferritins. This substantially reduces a risk of undesirable side effects of the vaccine after the host immunization.

Ticks with decreased synthesis of ferritin 2, caused by RNA interference, are not able to finish their feeding and usually dry and die directly on the host. This fact makes ferritin 2 an ideal candidate for development of vaccine or other compound that will interfere with ferritin 2. Disruption of the tick feeding on the immunized host can impair the normal tick development and possibly will lead to the elimination of pathogen transmission by ticks (e.g., Lyme disease spirochetes), which are dependent on the successful tick feeding.

EXAMPLES

Example 1

Ferritin 2, designated as FER2-IR, is a protein produced by the tick *Ixodes ricinus* and its primary structure is determined by the amino-acid sequence:

(SEQ ID. NO: 1)

MKQFVVILALIGAATSGNNLFENLDKYPLQDECQAALQEHINVEMHAS

LVYMQMAAHFDNNKVARKGFSTFFAENSKEEREHAQKIIDYINKRGST

VSLVNIDMPLITTWKSVLQALRDAISLENKVTNKLHAVHKIADEECKD

PQLMDFIESEFLEEQVNSIDKLQRMITVLSNMDSGTGEYLLDRELLGD

KKEF.

The signal sequence responsible for the protein secretion of the cell is marked in bold. The primary sequence enables correct folding of the protein to the quarter structure, which transports the non-heme iron from the tick gut to the peripheral tissues. In the absence of ferritin 2, or in the case of its successful blocking, the ticks are not able to finish feeding and dry directly on the host.

Example 2

Ferritin 2, designated as FER2-IS, is a protein produced by the tick Ixodes scapularis and its primary structure is determined by the amino-acid sequence.

(SEQ ID. NO: 2)

MKQFVVLLALIGAATSGNNLFENLDKYPLQDECQAALQEHINVEMHA

SLVYMQMAAHFDNNKVARKGFSTFFAENSKEEREHAQKIIDYINKRG

STVSLVNIDMPQITTWKSVLQALRDAISLENKVTNKLHAVHKTADEE

CKDPQLMDFIESEFLEEQVTSIDKLQRMITVLSNMDSGTGEYLLDRE

LLGDKKEF.

The signal sequence responsible for the protein secretion of the cell is marked in bold. The primary sequence enables correct folding of the protein to the quarter structure, which transports the non-heme iron from the tick gut to the peripheral tissues. In the absence of ferritin 2, or in the case of its successful blocking, the ticks are not able to finish feeding and dry directly on the host.

Example 3

Ferritin 2, designated as FER2-RM, is a protein produced by the tick *Rhipicephalus microplus* and its primary structure is determined by the amino-acid sequence:

(SEQ ID. NO: 3)
MLRIVLVVLAASVALAGNNLNDQVNKYILPDRCRAGLQEQLNLELHAS
LVYMQMAAHLANNKVARGGFARFFRDQSSEEREHAQKIIDYLNLRGGT
VSAVNVDMPPTAIWMSVLDALQAALALEHRVTNRLYELHRLAEEYDAQ
MADFLEQEFLAEQVRSIDQLQRLITQLQNMETGLGEFLLDQQLRA.

The signal sequence responsible for the protein secretion of the cell is marked in bold. The primary sequence enables correct folding of the protein to the quarter structure, which transports the non-heme iron from the tick gut to the peripheral tissues. In the absence of ferritin 2, or in the case of its successful blocking, the ticks are not able to finish feeding and dry directly on the host.

Example 4

Ferritin 2, designated as FER2-DV, is a protein produced by the tick Dermacentor variabilis and its primary structure is determined by the amino-acid sequence:

(SEQ ID. NO: 4)
**MLRLALL

<211> LENGTH: 196
<212> TYPE: PRT
<213> ORGANISM: Ixodes scapularis

<400> SEQUENCE: 2

Met Lys Gln Phe Val Val Leu Leu Ala Leu Ile Gly Ala Ala Thr Ser
1               5                   10                  15

Gly Asn Asn Leu Phe Glu Asn Leu Asp Lys Tyr Pro Leu Gln Asp Glu
            20                  25                  30

Cys Gln Ala Ala Leu Gln Glu His Ile Asn Val Glu Met His Ala Ser
                35                  40                  45

Leu Val Tyr Met Gln Met Ala Ala His Phe Asp Asn Asn Lys Val Ala
    50                  55                  60

Arg Lys Gly Phe Ser Thr Phe Phe Ala Glu Asn Ser Lys Glu Glu Arg
65                  70                  75                  80

Glu His Ala Gln Lys Ile Ile Asp Tyr Ile Asn Lys Arg Gly Ser Thr
                85                  90                  95

Val Ser Leu Val Asn Ile Asp Met Pro Gln Ile Thr Thr Trp Lys Ser
            100                 105                 110

Val Leu Gln Ala Leu Arg Asp Ala Ile Ser Leu Glu Asn Lys Val Thr
        115                 120                 125

Asn Lys Leu His Ala Val His Lys Thr Ala Asp Glu Glu Cys Lys Asp
130                 135                 140

Pro Gln Leu Met Asp Phe Ile Glu Ser Glu Phe Leu Glu Glu Gln Val
145                 150                 155                 160

Thr Ser Ile Asp Lys Leu Gln Arg Met Ile Thr Val Leu Ser Asn Met
                165                 170                 175

Asp Ser Gly Thr Gly Glu Tyr Leu Leu Asp Arg Glu Leu Leu Gly Asp
            180                 185                 190

Lys Lys Glu Phe
        195

<210> SEQ ID NO 3
<211> LENGTH: 189
<212> TYPE: PRT
<213> ORGANISM: Rhipicephalus microplus

<400> SEQUENCE: 3

Met Leu Arg Ile Val Leu Val Val Leu Ala Ala Ser Val Ala Leu Ala
1               5                   10                  15

Gly Asn Asn Leu Asn Asp Gln Val Asn Lys Tyr Ile Leu Pro Asp Arg
            20                  25                  30

Cys Arg Ala Gly Leu Gln Glu Gln Leu Asn Leu Glu Leu His Ala Ser
                35                  40                  45

Leu Val Tyr Met Gln Met Ala Ala His Leu Ala Asn Asn Lys Val Ala
    50                  55                  60

Arg Gly Gly Phe Ala Arg Phe Phe Arg Asp Gln Ser Ser Glu Glu Arg
65                  70                  75                  80

Glu His Ala Gln Lys Ile Ile Asp Tyr Leu Asn Leu Arg Gly Gly Thr
                85                  90                  95

Val Ser Ala Val Asn Val Asp Met Pro Pro Thr Ala Ile Trp Met Ser
            100                 105                 110

Val Leu Asp Ala Leu Gln Ala Ala Leu Ala Leu Glu His Arg Val Thr
        115                 120                 125

Asn Arg Leu Tyr Glu Leu His Arg Leu Ala Glu Glu Tyr Asp Ala Gln
130                 135                 140

-continued

```
Met Ala Asp Phe Leu Glu Gln Glu Phe Leu Ala Glu Gln Val Arg Ser
145                 150                 155                 160

Ile Asp Gln Leu Gln Arg Leu Ile Thr Gln Leu Gln Asn Met Glu Thr
                165                 170                 175

Gly Leu Gly Glu Phe Leu Leu Asp Gln Gln Leu Arg Ala
            180                 185
```

<210> SEQ ID NO 4
<211> LENGTH: 192
<212> TYPE: PRT
<213> ORGANISM: Dermacentor variabilis

<400> SEQUENCE: 4

```
Met Leu Arg Leu Ala Leu Leu Ile Ala Leu Ala Ser Ala Ala Trp Ala
1               5                   10                  15

Gly Asn Asn Leu Asn Glu Gln Val Asn Gln Asn Arg Tyr Phe Leu His
                20                  25                  30

Asp Arg Cys Arg Ile Gly Leu Gln Glu Gln Val Asn Leu Glu Leu His
            35                  40                  45

Ala Ser Leu Val Tyr Met Gln Met Ala Ala His Leu Ala Asn Asn Lys
        50                  55                  60

Val Ala Arg Asn Gly Phe Ala Arg Phe Phe Arg Asp Gln Ser Ser Glu
65                  70                  75                  80

Glu Arg Glu His Ala Gln Lys Leu Val Asp Tyr Val Asn Leu Arg Gly
                85                  90                  95

Gly Thr Val Ser Ala Val Ser Val Asp Met Pro Ala Thr Ala Thr Trp
            100                 105                 110

Met Ser Val Leu Asp Ala Leu Gln Ala Ala Leu Ala Leu Glu His Arg
        115                 120                 125

Val Thr Asn Arg Leu His Glu Leu His Arg Leu Ala Asp Asp Ser Gln
130                 135                 140

Asp Pro Gln Met Ala Asp Phe Leu Glu Gln Glu Phe Leu Ala Glu Gln
145                 150                 155                 160

Val Arg Ser Ile Asp Gln Leu Gln Arg Leu Ile Thr Gln Leu Gln Asn
                165                 170                 175

Met Asp Thr Gly Leu Gly Glu Phe Leu Leu Asp Gln Gln Leu Arg Ala
            180                 185                 190
```

What is claimed is:

1. Ferritin 2, isolated and purified from an expression system, for host immunization against ticks which has the amino-acid sequence without the signal sequence at least 85% identical to the amino-acid sequences of SEQ ID NO: 1.

2. Ferritin 2 for host immunization against ticks according to the claim 1, which consists of the amino-acid sequence of SEQ ID NO: 1.

3. Ferritin 2 for host immunization against ticks according to the claim 1, which consists of the amino-acid sequence of SEQ ID NO. 2.

* * * * *